(12) United States Patent
Fan

(10) Patent No.: US 7,446,098 B2
(45) Date of Patent: *Nov. 4, 2008

(54) COMBINATION THERAPY FOR TREATING PROTEIN DEFICIENCIES

(75) Inventor: Jian-Qiang Fan, Demarest, NJ (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/781,356

(22) Filed: Feb. 17, 2004

(65) Prior Publication Data

US 2004/0219132 A1 Nov. 4, 2004

Related U.S. Application Data

(60) Provisional application No. 60/448,073, filed on Feb. 18, 2003.

(51) Int. Cl.
*A61K 31/715* (2006.01)
*A61K 31/445* (2006.01)
*A61K 31/70* (2006.01)
*A61K 31/435* (2006.01)
*C12N 9/40* (2006.01)

(52) U.S. Cl. .................. 514/44; 514/315; 514/277; 514/25; 435/208

(58) Field of Classification Search ........... 514/44, 514/315
See application file for complete search history.

(56) References Cited

U.S. PATENT DOCUMENTS 6,051,598 A    4/2000  Shayman et al.
6,066,626 A *  5/2000  Yew et al. ............... 514/44
6,200,812 B1   3/2001  Pati et al.
6,255,113 B1   7/2001  Zarling et al.
6,274,597 B1 * 8/2001  Fan et al. ............... 514/315
6,589,964 B2 * 7/2003  Fan et al. ............... 514/315
6,599,919 B2 * 7/2003  Fan et al. ............... 514/315
6,774,135 B2 * 8/2004  Fan et al. ............... 514/315
2002/0035072 A1  3/2002  Fan et al.
2004/0204379 A1 10/2004  Cheng et al.

OTHER PUBLICATIONS

Verma et al (Nature 389:239-242, 1997) ☐☐.*
Anderson (Nature 392:25-30, 1998) ☐☐.*
Romano et al (Stem Cells 18: 19-39, 2000) ☐☐.*
Somia and Verma (Nature Reviews Genetics 1: 91-99, 2000).*
Rosenfeld and Collins (Chest 109:241-252, 1996).*
Rosenecker (Eur. J. Med. 23(3): 149-156, Mar. 1998).*
Boucher (TIG 1.2(3): 81-84, 1996, p. 81, paragraph bridging columns 2 and 3).*
Alton and Geddes (J. R. Soc. Med 90 Suppl 31: 43-46 1997).*
Davies (Mol. Med Today 4(7): 292-299, Jul. 1998, pp. 294, col. 2, lines 20-28).*
Boucher (J. Clin. Invest. 103(4): 441-445 Feb. 1999).*
Wilson (J. Clin. Invest. 96: 2547-2554, 1995).*
Ferrari et al (Adv. Drug Del. Rev 54:1373-1393, 2002).*
Fan (Trends in Pharm. Sci. 24(7): 355-360, 2003).*
Hendricks et al (Blood 96 (11 part 1): 845a, 2000).*
Handa et al (Dermatology 200: 262-265, 2000).*
Handa et al., 2000, "A case of symptomatic heterozygous female Fabry's disease without detectable mutation in the alpha-galactosidase gene," Dermatology 200:262-265.

* cited by examiner

*Primary Examiner*—Richard Schnizer
(74) *Attorney, Agent, or Firm*—Baker Botts LLP

(57) ABSTRACT

This application provides methods of improving gene therapy by combining gene therapy with active site-specific chaperones (ASSCs). The ASSC increases the stability and efficiency of the protein encoded by the recombinant gene that is administered.

40 Claims, No Drawings

COMBINATION THERAPY FOR TREATING PROTEIN DEFICIENCIES

This application claims priority from U.S. Provisional Application Ser. No. 60/448,073, filed Feb. 18, 2003, the disclosure of which is herein incorporated by reference in its entirety.

FIELD OF THE INVENTION

This invention relates to methods of treating protein deficiencies by combining gene therapy with an active site-specific chaperone (ASSC) for the protein encoded by the therapeutic gene. The invention further relates to compositions comprising the nucleic acid sequence containing the coding region of the gene and an ASSC for the encoded gene product.

BACKGROUND

Protein Deficiency

Proteins are synthesized intracellularly according to the genomic nucleotide sequence of a particular gene through transcription, translation, and other processes. Protein deficiency can be caused by a mutation in the coding gene, which results in (i) non-synthesis of the protein; (ii) synthesis of the protein which lacks biological activity; or (iii) synthesis of the protein containing normal or partial biological activity, but which cannot be appropriately processed to reach the native compartment of the protein. Protein deficiency disorders that result from genetic mutations are also referred to as genetic disorders. Certain DNA mutations result in amino acid substitutions that further impede, and in many cases preclude, proper folding of the mutant proteins.

In addition to protein deficiencies resulting from genetic mutations, some protein deficiencies arise due to a disease, or as a side effect of a treatment for a disease (e.g., chemotherapy) or as a result of nutritional insufficiency.

Current therapies. One current therapy for treating such disorders is protein replacement therapy, which typically involves intravenous, subcutaneous or intramuscular infusion of a purified form of the corresponding wild-type protein, or implantation of the enzyme in a bio-erodable solid form for extended-release. Protein replacement therapy has several caveats, such as difficulties with large-scale generation and purification of properly folded, glycosylated native protein, failure to achieve sufficient protein levels to ameliorate the deficiency, generation of an anti-protein immune response, and inability of proteins to cross the blood-brain barrier in diseases having significant central nervous system involvement. In addition, this therapy typically necessitates frequent, costly infusions or implantation due to short half-life of the administered protein in vivo.

Gene therapy involves replacing a defective or missing gene encoding by introducing a functional gene into somatic cells of an individual in need. Gene therapy can be accomplished by "ex vivo" methods, in which differentiated or somatic stem cells are removed from the individual's body, followed by the introduction of a normal copy of the defective gene into the explanted cells using a viral vector as the gene delivery vehicle. In addition, in vivo direct gene transfer technologies direct the therapeutic gene in situ using a broad range of viral vectors, liposomes, protein DNA complexes, naked DNA and other approaches in order to achieve a therapeutic outcome.

Although promising, gene therapy is also limited by technical difficulties, such as the inability of vectors to infect or transduce dividing cells, low expression of the target gene, and regulation of expression once the gene is delivered. In order to achieve the therapeutic purpose, it is important to maintain high expression level of the protein for a sufficient time to obtain a physiologically effective amount of protein. Further, it is important to ensure delivery of the protein to the appropriate tissues. In addition, it has been shown that over-expression of recombinant protein in insect cells and mammalian cells causes accumulation of the protein in the ER (Hsu et al., Biotechnol. Prog. 1997; 13: 96-104), presumably because the over-production exceeds the capacity of the ER quality control system, and this result is expected to occur in vivo as well.

Although not yet approved for therapeutic treatment in the United States, gene therapies (both ex vivo and direct transfer) for numerous disorders are under investigation. Vectors and/or host cells and methods for gene therapy have been developed and are in pre-clinical or clinical stages of development (see U.S. Pat. No. 6,066,626 to Nelson et al.; and U.S. Pat. No. 5,911,983 to Barranger et al.). SRI International also has developed gene therapy using homologous recombination of exogenous sequences to correct gene mutations for genetic diseases (see U.S. Pat. Nos. 6,255,113 to Zarling et al.).

A third, relatively recent approach to treating enzyme protein deficiencies involves the use of small molecule inhibitors to reduce the natural substrate of the deficient protein, thereby ameliorating the pathology. This "substrate deprivation" approach has been specifically described for a class of about 40 related enzyme disorders called lysosomal storage disorders or glycosphingolipid storage disorders. These heritable, "conformational" disorders are characterized by deficiencies in lysosomal enzymes that catalyze the breakdown of glycolipids in cells, resulting in an abnormal accumulation of lipids, which disrupts cellular function. The small molecule inhibitors proposed for use as therapy are specific for inhibiting the enzymes involved in synthesis of glycolipids, reducing the amount of cellular glycolipid that needs to be broken down by the deficient enzyme. This approach is also limited in that glycolipids are necessary for biological function, and excess deprivation may cause adverse effects. Specifically, glycolipids are used by the brain to send signals from the gangliosides of neurons to other neurons. If there are too few or too many glycolipids, the ability of the neuron to send signals is impeded.

A fourth approach, discussed below, rescues mutant proteins from degradation in the endoplasmic reticulum.

Protein Folding and Processing in the Endoplasmic Reticulum

Proteins are synthesized in the cytoplasm, and the newly synthesized proteins are secreted into the lumen of the endoplasmic reticulum (ER) in a largely unfolded state. In general, protein folding is governed by the principle of self assembly. Newly synthesized polypeptides fold into their native conformation based on their amino acid sequences (Anfinsen et al., Adv. Protein Chem. 1975; 29:205-300). In vivo, protein folding is complicated, because the combination of ambient temperature and high protein concentration stimulates the process of aggregation, in which amino acids normally buried in the hydrophobic core interact with their neighbors non-specifically. To avoid this problem, protein folding is usually facilitated by a special group of proteins called molecular chaperones, which prevent nascent polypeptide chains from aggregating, and bind to unfolded protein such that the protein refolds in the native conformation (Hartl, Nature 1996; 381:571-580).

Molecular chaperones are present in virtually all types of cells and in most cellular compartments. Some are involved in the transport of proteins and permit cells to survive under stresses such as heat shock and glucose starvation. Among the molecular chaperones Bip (immunoglobulin heavy-chain binding protein, Grp78) is the best characterized chaperone of the ER (Haas, Curr. Top. Microbiol. Immunol. 1991; 167:71-82), but others are also known (Gething et al., Nature 1992; 355:33-45; Caplan, Trends Cell. Biol. 1999; 9:262-268; Lin et al., Mol. Biol. Cell. 1993; 4:109-1119; Bergeron et al., Trends Biochem. Sci. 1994; 19:124-128). Like other molecular chaperones, Bip interacts with many secretory and membrane proteins within the ER throughout their maturation, although the interaction is normally weak and short-lived when the folding proceeds smoothly. Once the native protein conformation is achieved, the molecular chaperone no longer interacts with the protein. Bip binding to a protein that fails to fold, assemble or be properly glycosylated becomes stable, and leads to degradation of the protein through the ER-associated degradation pathway. This process serves as a "quality control" system in the ER, ensuring that only those properly folded and assembled proteins are transported out of the ER for further maturation, and improperly folded proteins are retained for subsequent degradation (Hurtley et al., Annu. Rev. Cell. Biol. 1989; 5:277-307).

As stated above, certain DNA mutations result in amino acid substitutions that further impede, and in many cases preclude, proper folding of the mutant proteins. To correct these misfoldings, investigators have attempted to use various molecules. High concentrations of glycerol, dimethylsulfoxide (DMSO), trimethylamine N-oxide (TMAO), or deuterated water have been shown to suppress the degradation pathway and increase the intracellular trafficking of mutant protein in several diseases (Brown et al., Cell Stress Chaperones 1996; 1:117-125; Burrows et al., Proc. Natl. Acad. Sci. USA. 2000; 97:1796-801). These compounds are considered non-specific chemical chaperones to improve the general protein folding, although the mechanism of the function is still unknown. The high doses of this class of compounds required for efficacy makes them difficult or inappropriate to use clinically, although they are useful for the biochemical examination of folding defect of a protein intracellularly. These compounds also lack specificity.

Specific Chaperone Strategy

Previous patents and publications of the present inventor described a therapeutic strategy for rescuing endogenous enzyme proteins, specifically misfolded lysosomal enzymes, from degradation by the ER quality control machinery. This strategy employs small molecule reversible competitive inhibitors specific for a defective lysosomal enzyme associated with a particular lysosomal disorder. The strategy is as follows: since the mutant enzyme protein folds improperly in the ER (Ishii et al., Biochem. Biophys. Res. Comm. 1996; 220; 812-815), the enzyme protein is retarded in the normal transport pathway (ER→Golgi apparatus→endosome→lysosome) and rapidly degraded. Therefore, a functional compound which facilitates the correct folding of a mutant protein will serve as a site-specific chaperone for the mutant protein to promote the smooth escape from the ER quality control system. Since some inhibitors of an enzyme are known to occupy the catalytic center of enzyme, resulting in stabilization of its conformation in vitro. These specific chaperones may be designated active-site specific chaperones (ASSC).

The strategy has been specifically demonstrated for enzymes involved in the lysosomal storage disorders in U.S. Pat. Nos. 6,274,597, 6,583,158, 6,589,964, and 6,599,919, to Fan et al., which are hereby incorporated herein by reference in their entirety. For example, a small molecule derivative of galactose, 1-deoxygalactonojirimycin (DGJ), a potent competitive inhibitor of the mutant Fabry enzyme α-galactosidase A (α-Gal A), effectively increased in vitro stability of a mutant αa-Gal A (R301Q) at neutral pH and enhanced the mutant enzyme activity in lymphoblasts established from Fabry patients with R301Q or Q279E mutations. Furthermore, oral administration of DGJ to transgenic mice overexpressing a mutant (R301Q) α-Gal A substantially elevated the enzyme activity in major organs (Fan et al., Nature Med. 1999; 5: 112-115). Successful rescue of a misfolded protein depends on achieving a concentration of the specific inhibitor in vivo that is lower than necessary to completely inhibit the enzyme, in contrast to the substrate deprivation approach in which enzyme inhibitory concentrations are required.

In addition to the lysosomal storage disorders, a large and diverse number of diseases are now recognized as conformational diseases that are caused by adoption of non-native protein conformations, which may lead to retardation of the protein in the ER and ultimate degradation of the proteins (Kuznetsov et al., N. Engl. J. Med. 1998; 339:1688-1695; Thomas et al., Trends Biochem. Sci. 1995; 20:456-459; Bychkova et al., FEBS Lett. 1995; 359:6-8; Brooks, FEBS Lett. 1997; 409:115-120). ASSCs have been shown to rescue expression of mutant proteins other than enzymes. For example, small synthetic compounds were found to stabilize the DNA binding domain of mutant forms of the tumor suppressor protein p53, thereby allowing the protein to maintain an active conformation (Foster et al., Science 1999; 286: 2507-10). Synthesis of receptors has been shown to be rescued by small molecule receptor antagonists and ligands (Morello et al., J. Clin. Invest. 2000; 105: 887-95; Petaja-Repo et al., EMBO J. 2002; 21:1628-37.) Even pharmacological rescue of membrane channel proteins and other plasma membrane transporters has been demonstrated using channel-blocking drugs or substrates (Rajamani et al., Circulation 2002; 105:2830-5; Zhou et al., J. Biol. Chem. 1999; 274:31123-26; Loo et al., J. Biol. Chem 1997; 272: 709-12). All of the above references indicate that ASSC's are capable of specific rescue of mutant proteins including, but not limited to, enzymes, receptors, membrane channel proteins, and DNA transcription factors.

In addition to mutant proteins, ASSCs have also been shown to stabilize wild-type proteins, resulting in their enhanced production and stability. As one example, it has been demonstrated that a specific ASSC, DGJ, is able to increase the amount and activity of wild-type α-Gal A in COS-7 cells transfected with a vector coding the wild-type α-Gal A sequence. The ASSC rescues the overexpressed wild-type enzyme, which is otherwise retarded in the ER quality control system, because overexpression and over production of the enzyme in the COS-7 cells exceeds the capacity of the system and leads to aggregation and degradation (see U.S. application Ser. No. 10/377,179, filed Feb. 28, 2003).

However, effective in rescuing conformationally defective proteins, ASSCs cannot rescue proteins that are not make, e.g., as a result of a deletion mutation or nonsense mutation. Treatment of these conditions requires either replacing the protein (through protein replacement or gene therapy) or inhibition of accumulated product synthesis. Gene therapy holds great promise for long-term relief and mitigation of undesirable side effects. However, as discussed above, gene therapy has not yet reached sufficient efficiency to become a widespread therapy.

In summary, there is a need in the art for methods of improving the biological and cost efficiency of gene therapy in the treatment of protein deficiencies or other disorders where gene therapy is applied. The present invention addresses this need by adapting a technology already proven to increase the efficiency of gene expression to in vivo gene therapy.

SUMMARY OF THE INVENTION

The present invention provides a method of treatment for an individual having a disorder treatable by gene therapy. The method comprises administering to the individual a replacement gene and an ASSC for the protein encoded by the administered gene.

The present invention also provides a method for enhancing the stability of a protein encoded by the administered gene in vivo, comprising contacting the protein in vivo with an ASSC.

The invention further provides a method for increasing the expression by a target cell of a recombinant protein encoded by the gene being administered in vivo by administering an ASSC for the recombinant protein.

The invention also provides a method for enhancing the stability of a mutant, endogenous protein that is deficient due to defective folding or processing in the ER. Stability and, hence, activity of the endogenous protein will be enhanced concurrently with the increased stability of the protein produced by the administered gene.

The invention further provides a composition comprising an ASSC for the recombinant protein expressed by the gene in a pharmaceutically acceptable carrier.

DETAILED DESCRIPTION

The present invention improves the efficiency of gene therapy for protein deficiencies by combining standard gene therapy approaches with an active site-specific chaperone (ASSC), i.e., an agent capable of inducing the proper/native folding conformation of the protein, and stabilizing the protein encoded by the gene. The ASSC enhances the in vivo expression, efficiency, and stability of the expressed protein. The invention further provides formulations comprising a recombinant gene and an ASSC specific for the induction of the proper/native folding conformation of the protein and stabilization of the protein encoded by the gene. The invention is based on the discovery that ASSCs can be used as a combination therapy with gene therapy for the treatment of genetic disorders and other disorders. Although previous studies have demonstrated the ability of ASSCs to increase the level of expression of a normal, wild-type protein in tissue culture, modifying expression levels in artificial systems does not establish that one can achieve this result for a wild-type therapeutic protein in vivo. It has now been recognized that, instead, the in vivo methods for rescuing defective misfolded proteins can be modified as set forth herein to improve the efficiency of expression of a therapeutic (wild-type) protein delivered through gene therapy.

ASSCs can be screened and identified using methods known in the art. Once an ASSC useful for a particular disorder is identified, the chaperone can be administered to a patient receiving gene therapy. The ASSC can supplement endogenous molecular chaperones during high level expression of the therapeutic gene to increase the efficiency of expression by inhibiting aggregation in the ER. The chaperone can also as a stabilizer to prevent the degradation of the encoded protein being produced by the administered gene.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

Specific Definitions. The term "gene therapy" refers to a method of changing the expression of an endogenous gene by exogenous administration of a gene. As used herein, gene therapy also refers to the replacement of defective gene encoding a defective protein, or replacement of a missing gene, by introducing a functional gene corresponding to the defective or missing gene into somatic or stem cells of an individual in need. Gene therapy can be accomplished by "ex vivo" methods, in which differentiated or somatic stem cells are removed from the individual's body followed by the introduction of a normal copy of the defective gene into the explanted cells using a viral vector as the gene delivery vehicle. In addition, in vivo direct gene transfer technologies gene transfer into cells in the individual in situ using a broad range of viral vectors, liposomes, protein DNA complexes or naked DNA in order to achieve a therapeutic outcome.

The term "stabilize a proper conformation" refers to the ability of a compound or peptide or other molecule to associate with a wild-type protein, or to a mutant protein that can perform its wild-type function in vitro in, e.g., a formulation and in vivo, in such a way that the structure of the wild-type or mutant protein can be maintained as its native or proper form. This effect may manifest itself practically through one or more of (i) increased shelf-life of the protein; (ii) higher activity per unit/amount of protein; or (iii) greater in vivo efficacy. It may be observed experimentally through increased yield from the ER during expression; greater resistance to unfolding due to temperature increases, or the present of chaotropic agents, and by similar means.

The present invention enhances the efficacy of gene therapy by increasing the level of expression of the therapeutic gene in vivo. As used herein, "increasing the level of expression" means increasing the amount of recombinant protein, the quality of recombinant protein (i.e., the yield of functional protein), the level of protein activity, or any combination of the foregoing, in a cell contacted with an ASSC relative to that value in the same type of cell not contacted with the ASSC. The degree of increased expression is not important, since even modest increases can have dramatic effects, but will generally be greater than about 20%, preferably greater than about 50%, and more preferably at least about 100%.

The term "recombinant protein" refers to a protein (gene product) encoded by a therapeutic gene carried on a vector. Generally, the cell receiving the vector will lack expression of any endogenous protein corresponding to the recombinant protein, or if there is expression of such an endogenous protein, it is of a mutant or at a very low level. The recombinant protein will likely be indistinguishable from wild-type protein in normal individuals, i.e., individuals who are not deficient in the protein.

The term "disorder characterized by a protein deficiency" refers to any disorder that presents with a pathology caused by absent or insufficient amounts of a protein. This term encompasses protein folding disorders, i.e., conformational disorders, that result in a biologically inactive protein product. Protein insufficiency can be involved in infectious diseases, immunosuppression, organ failure, glandular problems, radiation illness, nutritional deficiency, poisoning, or other environmental or external insults.

As used herein, the term "conformational disorder" or "conformational disease" refers to a disorder that is caused by adoption of a protein conformation that is not normally formed by a wild-type protein in a native condition with normal biological activity, which may lead to retardation and destruction of a protein in the ER. The decreased protein level results in a physiological imbalance that manifests itself as a disease or disorder.

As used herein, the term "active site" refers to the region of a protein that performs some specific biological function. For example, it can be a site that binds a substrate or other binding partner and contributes the amino acid residues that directly participate in the making and breaking of chemical bonds. Active sites in this invention can encompass catalytic sites of enzymes, antigen biding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "active site-specific chaperone" refers to any molecule including a protein, peptide, nucleic acid, carbohydrate, etc. that specifically interacts reversibly with an active site of a protein and enhances formation of a stable molecular conformation. As used herein, "active site-specific chaperone" does not include endogenous general chaperones present in the ER of cells such as Bip, calnexin or calreticulin, or general, non-specific chemical chaperones such as deuterated water, DMSO, or TMAO.

General Definitions. The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for administration to a human or non-human animal.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

A "gene" is a sequence of nucleotides which code for a functional "gene product". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also said to be "expressed" by the cell.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, and expression systems, and mammalian host cells and vectors.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

As used herein the term "mutant protein" refers to proteins translated from genes containing genetic mutations that result in altered protein sequences. In a specific embodiment, such mutations result in the inability of the protein to achieve its native conformation under the conditions normally present in the ER. The failure to achieve this conformation results in these proteins being degraded, rather than being transported through their normal pathway in the protein transport system to their proper location within the cell. Other mutations can result in decreased activity or more rapid turnover.

A "wild-type gene" refers to a nucleic acid sequences which encodes a protein capable of having functional biological activity in vivo. The wild-type nucleic acid sequence may contain nucleotide changes that differ from the known, published sequence of the as long as the changes result in conservative amino acid substitutions having little or no effect on the biological activity. As used herein, the term wild-type may also include nucleic acid sequences engineered to encoding a protein capable of increased or enhanced activity relative to the endogenous or native protein.

A "wild-type protein" refers to any protein encoded by a wild-type gene that is capable of having functional biological activity when expressed or introduced in vivo. The term "normal wild-type activity" refers to the normal physiological function of a protein in a cell. Such functionality can be tested by any means known to establish functionality of a protein.

The term "normal wild-type activity" refers to the normal physiological function of a protein in a cell. Such functionality can be tested by any means known to establish functionality of a protein. This effect may manifest itself practically through one or more of (i) higher activity per unit/amount of protein; or (ii) greater in vivo efficacy. It may be observed experimentally through increased yield from the ER during expression; greater resistance to unfolding due to temperature increases, or the present of chaotropic agents, and by similar means.

The term "genetically modified" refers to cells that express a particular gene product following introduction of a nucleic acid comprising a coding sequence which encodes the gene product, along with regulatory elements that control expression of the coding sequence. Introduction of the nucleic acid may be accomplished by any method known in the art including gene targeting and homologous recombination.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

The phrase "pharmaceutically acceptable", whether used in connection with the pharmaceutical compositions of the invention, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "therapeutically effective dose" and "effective amount" as used herein means an amount of ASSC that enhances without inhibiting the activity of the protein for which the ASSC is specific, i.e., an effective amount enhances more than it inhibits so the net effect is an enhancement. For example, in the case of an enzyme, where the ASSC is a specific inhibitor of the enzyme, an effective amount will be an amount of the inhibitor effective to increase the level of expression of the enzyme without actually inhibiting the enzyme. This will generally fall somewhere below the $IC_{50}$ value of that inhibitor for the enzyme. Similar values can be determined for receptors with chaperone ligands, hormones with chaperone receptors, and the like.

It should be noted that a concentration of the ASSC that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the ASSC upon administration in vivo.

Disorders Characterized by Protein Deficiencies

There currently are about 1100 known inherited disorders characterized by protein deficiency or loss-of-function in a specific tissue. These disorders may be treatable by gene therapy in theory. The method of the present invention contemplates co-therapy for proteins currently suited for use in gene therapy that is available now or will be in the future. In such disorders, certain cells or all of the cells of an individual lack a sufficient functional protein, contain an inactive form of the protein or contain insufficient levels of the protein for biological function.

Further, the list of diseases identified as being conformational disorders, caused by mutations that alter protein folding and retardation of the mutant protein in the ER, resulting in protein deficiency, is increasing. These include cystic fibrosis, α1-antitrpsin deficiency, familial hypercholesterolemia, Alzheimer's disease (Selkoe, Annu. Rev. Neurosci. 1994; 17:489-517), osteogenesis imperfecta (Chessler et al., J. Biol. Chem. 1993; 268:18226-18233), carbohydrate-deficient glycoprotein syndrome (Marquardt et al., Eur. J. Cell. Biol. 1995; 66: 268-273), Maroteaux-Lamy syndrome (Bradford et al., Biochem. J. 1999; 341:193-201), hereditary blindness (Kaushal et al., Biochemistry 1994; 33:6121-8), Glanzmann thrombasthenia (Kato et al., Blood 1992; 79:3212-8), hereditary factor VII deficiency (Arbini et al., Blood 1996; 87:5085-94), oculocutaneous albinism (Halaban et al., Proc. Natl. Acad. Sci. USA. 2000; 97:5889-94) and protein C deficiency (Katsumi, et al., Blood 1996; 87:4164-75). Recently, one mutation in the X-linked disease adrenoleukodystrophy (ALD) resulted in misfolding of the defective peroxisome transporter, which could be rescued by low-temperature cultivation of affected cells (Walter et al., Am. J. Hum. Genet. 2001;69:35-48). It is generally accepted that mutations take place evenly over the entire sequence of a gene. Therefore, it is predictable that the phenotype resulting from protein deficiencies exists in many other genetic disorders.

Lysosomal Storage Disorders

Many of the inherited protein deficient disorders are enzyme deficiencies. As indicated above, a large class of inherited enzyme disorders involve mutations in lysosomal enzymes and are referred to as lysosomal storage disorders (LSDs). Lysosomal storage disorders are a group of diseases caused by the accumulation of glycosphingolipids, glycogen, mucopolysaccharides Examples of lysosomal disorders include Gaucher disease (Beutler et al., *The Metabolic and Molecular Bases of Inherited Disease, 8th ed.* 2001 Scriver et al., ed. pp. 3635-3668, McGraw-Hill, New York), GM1-gangliosidosis (id. at pp 3775-3810), fucosidosis (*The Metabolic and Molecular Bases of Inherited Disease* 1995. Scriver, C. R., Beaudet, A. L., Sly, W. S. and Valle, D., ed pp. 2529-2561, McGraw-Hill, New York), mucopolysaccharidoses (id. at pp 3421-3452), Pompe disease (id. at pp. 3389-3420), Hurler-Scheie disease (Weismann et al., Science 1970; 169, 72-74), Niemann-Pick A and B diseases, (*The Metabolic and Molecular Bases of Inherited Disease* 8*th ed.* 2001. Scriver et al. ed., pp 3589-3610, McGraw-Hill, New York), and Fabry disease (id. at pp. 3733-3774). A list of LSDs and their associated deficient enzymes can be found in Table 1 below. Two are discussed specifically infra.

about 1:40,000 in males, and is reported throughout the world within different ethnic groups. In classically affected males, the clinical manifestations include angiokeratoma, acroparesthesias, hypohidrosis, and characteristic corneal and lenticular opacities (*The Metabolic and Molecular Bases of Inherited Disease, 8$^{th}$ Edition* 2001, Scriver et al., ed., pp. 3733-3774, McGraw-Hill, New York). The affected male's life expectancy is reduced, and death usually occurs in the

TABLE 1

Lysosomal Storage Disorders, Defective Enzymes Associated Therewith, and Reversible Active Site Specific Chaperones

| DISORDER | DEFICIENT ENZYME | REVERSIBLE CHAPERONE |
|---|---|---|
| Pompe disease | α-Glucosidase | 1-deoxynojirimycin (DNJ) |
|  |  | α-homonojirimycin |
|  |  | castanospermine |
| Gaucher disease | Acid β-Glucosidase | isofagomine |
|  | (glucocerebrosidase) | N-dodecyl-DNJ |
|  |  | calystegines $A_3$, $B_1$, $B_2$ and $C_1$ |
| Fabry disease | α-Galactosidase A | 1-deoxygalactonojirimycin (DGJ) |
|  |  | α-allo-homonojirimycin |
|  |  | α-galacto-homonojirimycin |
|  |  | β-1-C-butyl-deoxynojirimycin |
|  |  | calystegines $A_2$ and $B_2$ |
|  |  | N-methyl calystegines $A_2$ and $B_2$ |
| $G_{M1}$-gangliosidosis | Acid β-Galactosidase | 4-epi-isofagomine |
|  |  | 1-deoxygalactonojirimycin |
| Krabbe disease | Galactocerebrosidase | 4-epi-isofagomine |
|  |  | 1-deoxygalactonojirimycin |
| Morquio disease B | Acid β-Galactosidase | 4-epi-isofagomine |
|  |  | 1-deoxygalactonojirimycin |
| α-Mannosidosis | Acid α-Mannosidase | 1-deoxymannojirimycin |
|  |  | Swainsonine |
|  |  | Mannostatin A |
| β-Mannosidosis | Acid β-Mannosidase | 2-hydroxy-isofagomine |
| Fucosidosis | Acid α-L-fucosidase | 1-deoxyfuconojirimycin |
|  |  | β-homofuconojirimycin |
|  |  | 2,5-imino-1,2,5-trideoxy-L-glucitol |
|  |  | 2,5-deoxy-2,5-imino-D-fucitol |
|  |  | 2,5-imino-1,2,5-trideoxy-D-altritol |
| Sanfilippo disease B | α-N-Acetylglucosaminidase | 1,2-dideoxy-2-N-acetamido-nojirimycin |
| Schindler disease | α-N-Acetylgalactosaminidase | 1,2-dideoxy-2-N-acetamido-galactonojirimycin |
| Tay-Sachs disease | β-Hexosaminidase A | 2-N-acetylamino-isofagomine |
|  |  | 1,2-dideoxy-2-acetamido-nojirimycin |
|  |  | nagstain |
| Sandhoff disease | β-Hexosaminidase B | 2-N-acetamido-isofagomine, nagstein |
|  |  | 1,2-dideoxy-2-acetamido-nojirimycin |
| Hurler-Scheie disease | α-L-Iduronidase | 1-deoxyiduronojirimycin |
|  |  | 2-carboxy-3,4,5-trideoxypiperidine |
| Sly disease | β-Glucuronidase | 6-carboxy-isofagomine |
|  |  | 2-carboxy-3,4,5-trideoxypiperidine |
| Sialidosis | Sialidase | 2,6-dideoxy-2,6, imino-sialic acid |
|  |  | Siastatin B |
| Hunter disease | Iduronate sulfatasee | 2,5-anhydromannitol-6-sulphate |
| I-cell disease | N-acetylglucosamine-1-phosphotransferase |  |
| Niemann-Pick disease | Acid sphingomyelinase | desipramine, phosphatidylinositol-4,5-diphosphate |

Fabry disease

Fabry disease is an X-linked inborn error of glycosphingolipid metabolism caused by deficient lysosomal α-galactosidase A (α-Gal A) activity (Desnick et al., *The Metabolic and Molecular Bases of Inherited Disease, 8$^{th}$ Edition* Scriver et al. ed., pp. 3733-3774, McGraw-Hill, New York 2001; Brady et al., N. Engl. J. Med. 1967; 276, 1163-1167). This enzymatic defect leads to the progressive deposition of neutral glycosphingolipids with α-galactosyl residues, predominantly globotriaosylceramide (GL-3), in body fluids and tissue lysosomes. The frequency of the disease is estimated to be fourth or fifth decade as a result of vascular disease of the heart, brain, and/or kidneys. In contrast, patients with the milder "cardiac variant" normally have 5-15% of normal α-Gal A activity, and present with left ventricular hypertrophy or a cardiomyopathy. These cardiac variant patients remain essentially asymptomatic when their classically affected counterparts are severely compromised. Recently, cardiac variants were found in 11% of adult male patients with unexplained left ventricular hypertrophic cardiomyopathy, suggesting that Fabry disease may be more frequent than previously estimated (Nakao et al., N. Engl. J. Med. 1995;

333, 288-293). The α-Gal A gene has been mapped to Xq22, (Bishop et al., Am. J. Hum. Genet. 1985; 37: A144), and the full-length cDNA and entire 12-kb genomic sequences encoding α-Gal A have been reported (Calhoun et al., Proc. Natl. Acad. Sci. USA 1985; 82; 7364-7368; Bishop et al., Proc. Natl. Acad. Sci. USA 1986; 83: 4859-4863; Tsuji et al., Eur. J. Biochem. 1987; 165; 275-280; and Kornreich et al., Nucleic Acids Res. 1989; 17: 3301-3302). There is a marked genetic heterogeneity of mutations that cause Fabry disease (*The Metabolic and Molecular Bases of Inherited Disease, 8th Edition* 2001, Scriver et al., ed., pp. 3733-3774, McGraw-Hill, New York.; Eng et al., Am. J. Hum. Genet. 1993; 53: 1186-1197; Eng et al., Mol. Med. 1997; 3: 174-182; and Davies et al., Eur. J. Hum. Genet. 1996; 4: 219-224). To date, a variety of missense, nonsense, and splicing mutations, in addition to small deletions and insertions, and larger gene rearrangements have been reported.

Gaucher Disease

Gaucher disease is a deficiency of the lysosomal enzyme β-glucocerebrosidase that breaks down fatty glucocerebrosides. The fat then accumulates, mostly in the liver, spleen and bone marrow. Gaucher disease can result in pain, fatigue, jaundice, bone damage, anemia and even death. There are three clinical phenotypes of Gaucher disease. Patients with, Type 1 manifest either early in life or in young adulthood, bruise easily and experience fatigue due to anemia, low blood platelets, enlargement of the liver and spleen, weakening of the skeleton, and in some instances have lung and kidney impairment. There are no signs of brain involvement. In Type II, early-onset, liver and spleen enlargement occurs by 3 months of age and there is extensive brain involvement. There is a high mortality rate by age 2. Type III is characterized by liver and spleen enlargement and brain seizures. The β-glucocerebrosidase gene is located on the human 1q21 chromosome. Its protein precursor contains 536 amino acids and its mature protein is 497 amino acids long.

Gaucher disease is considerably more common in the descendants of Jewish people from Eastern Europe (Ashkenazi), although individuals from any ethnic group may be affected. Among the Ashkenazi Jewish population, Gaucher disease is the most common genetic disorder, with an incidence of approximately 1 in 450 persons. In the general public, Gaucher disease affects approximately 1 in 100,000 persons. According to the National Gaucher Foundation, 2,500 Americans suffer from Gaucher disease.

Other Enzyme Deficiency Disorders

Glucose-6-phosphate dehydrogenase (G6PD) deficiency the most common X-linked human enzyme deficiency. The G6PD enzyme catalyzes an oxidation/reduction reaction that is essential for the production of ribose, which is an essential component of both DNA and RNA. G6PD also involved in maintaining adequate levels of NADPH inside the cell. NADPH is a required cofactor in many biosynthetic reactions. Individuals with this deficiency have clinical symptoms including neonatal jaundice, abdominal and/or back pain, dizziness, headache, dyspnea (irregular breathing), and palpitations.

One form of severe combined immunodeficiency (SCID) is due to lack of the enzyme adenosine deaminase (ADA), coded for by a gene on chromosome 20. This means that the substrates for this enzyme accumulate in cells. Immature lymphoid cells of the immune system are particularly sensitive to the toxic effects of these unused substrates, so fail to reach maturity. As a result, the immune system of the afflicted individual is severely compromised or completely lacking.

In addition to inherited disorders, other enzyme deficiencies arise from damage to a tissue or organ resulting from primary or secondary disorders. For example, damaged pancreatic tissue, or pancreatitis, is caused by alcoholism results in a deficiency in pancreatic enzymes necessary for digestion.

Other Disorders Treated Using Gene Therapy

There are numerous disorders involving defective genes other than enzymes involved in metabolic disorders that can be treated using gene therapy. Such disorder include but are not limed to severe combined immunodeficiency (SCID), phagocyte disorders such as Wiskott-Aldrich syndrome, bleeding disorders such as von Willebrand's disease and hemophilia, endocrine disorders such as growth hormone deficiency and hypothalamic diabetes insipidus, retinal degradation, cancers caused by inherited genetic defects such as heredetary non-polyposis colon cancer (HNPCC). Such disorders are listed in Table 2 below.

TABLE 2

DISORDERS TREATED USING GENE THERAPY

| DISORDER | REFERENCE |
|---|---|
| Ad5p53 in head and neck cancer | Burt et al. J Mol Med 1997; 75(5): B28 (86). |
| Ad5p53 in hematologic malignancies | Bishop et al. J Clin Oncol 1996 Apr;14(4): 1320-6. |
| ADA deficiency | Bordignon et al. Science 1995; 270: 470-475. |
| Adp53 in non-small cell lung cancer | Roth et al. Semin Oncol 1998 Jun;25(3 Suppl 8): 33-7. |
| BRCA1 in ovarian cancer | Tait et al. Clin Cancer Res 1999;5(7): 1708-14 |
| Chronic granulomatous disease | Malech et al. PNAS USA 94(22): 12133-8. |
| Cystic fibrosis | Gill et al. Gene Ther 1997; 4: 199-209. |
| Cytokine-transfected xenogeneic cells | Rochlitz et al. Adv Exp Med Biol 1998;451: 531-7. |
| Familial hypercholesterolemia | Grossmann et al. Nature Genet 1994; 6: 335-341. |
| Hemophilia B (factor IX deficiency) | Qiu et al. Chin Med J (Engl) 109: 832-839. |
| hypothalamic diabetes insipidus | Chin Med J (Engl) 109: 832-839 |
| IL-12 enhanced melanoma vaccination | Sun et al. Gene Ther 1998;5: 481-490. |
| IL-2 therapy of solid tumors | Stewart et al. Gene Ther 1999 Mar;6(3): 350-63. |
| IL-7 enhanced melanoma vaccination | Moller et al. Br J Cancer 1998 Jun;77(11):1907-16. |
| Liposome p53 in hepatocellular carcinoma | Habib et al. Cancer Detect Prev 20(2): 103-7 |
| Mucopolysaccharidosis | Stroncek et al. Transfusion 1999; 39(4): 343-50. |
| von Willebrand's disease | Wilcox et al., J Thromb Haemost.2003; 1: 2300-11 |
| Wiskott-Aldrich syndrome | Strom et al., Blood. 2003;102(9): 3108-16 |
| X-linked severe combined immunodeficiency | Marina et al. Science 2000; 288: 669-672. |

Treatment of Protein Deficiencies and Other Disorders

By overexpression of wild-type protein in suitable cells (e.g., stem cells or somatic tissue-specific cells) of an individual, using molecular biology techniques, the missing or deficient protein is produced in the cells, and in most cases circulates within the blood stream to the particular tissues. In order to achieve the therapeutic purpose, it is important to maintain high expression level of the protein for a sufficient time to confer a therapeutic benefit. Further, it is important to ensure specific delivery of the protein to the appropriate tissues.

Co-Therapy Using ASSCs and Gene Therapy

The present invention increases the effectiveness of gene therapy by increasing the folding and processing of the protein encoded by the gene administered during synthesis, and increasing the stability of the newly-synthesized protein in vivo by co-administration of an ASSC for the protein encoded by the administered gene. Screening for an appropriate ASSC for the target protein can be achieved by known methods in the art, e.g., as described in U.S. patent application Ser. No. 10/377,179, filed Feb. 28, 2003.

Gene Therapy

Disorders that can be treated using the method of the present invention include but are not limited to those mentioned above and those listed in Table 1. This method can be used in combination with any defective gene contemplated to be replaced using gene therapy. For example, the method can be used to provide secreted proteins, membrane proteins, or intracellular proteins.

Any of the methods for gene therapy available in the art can be used according to the present invention. Exemplary methods are described below. For general reviews of the methods of gene therapy, see Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260:926-932; and Morgan and Anderson, Ann. Rev. Biochem. 1993, 62:191-217; May, TIBTECH 1993, 11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY; Colosimo et al., Biotechniques 2000;29(2):314-8, 320-2, 324.

The gene to be administered for the methods of the present invention can be isolated and purified using ordinary molecular biology, microbiology, and recombinant DNA techniques within the skill of the art. For example, nucleic acids encoding the target protein can be isolated using recombinant DNA expression as described in the literature. See, e.g., Sambrook, Fritsch & Maniatis, *Molecular Cloning. A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. ÊHiggins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. ÊPerbal, *A Practical Guide To Molecular Cloning* (1984); F. M. Ausubel et al. (eds.), *Current Protocols in Molecular Biology*, John Wiley & Sons, Inc. (1994). The nucleic acid encoding the protein may be full-length or truncated, so long as the gene encodes a biologically active protein. For example, a biologically active, truncated form of α-Gal A, the defective enzyme associated with Fabry disease, has been described in U.S. Pat. No. 6,210,666 to Miyamura et al.

The identified and isolated gene can then be inserted into an appropriate cloning vector. Vectors suitable for gene therapy include viruses, such as adenoviruses, adeno-associated virus (AAV), vaccinia, herpesviruses, baculoviruses and retroviruses, parvovirus, lentivirus, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

In a preferred embodiment, the vector is a viral vector. Viral vectors, especially adenoviral vectors can be complexed with a cationic amphiphile, such as a cationic lipid, polyL-lysine (PLL), and diethylaminoethyldextran (DELAE-dextran), which provide increased efficiency of viral infection of target cells (See, e.g., PCT/US97/21496 filed Nov. 20, 1997, incorporated herein by reference). Preferred viral vectors for use in the present invention include vectors derived from vaccinia, herpesvirus, AAV and retroviruses. In particular, herpesviruses, especially herpes simplex virus (HSV), such as those disclosed in U.S. Pat. No. 5,672,344, the disclosure of which is incorporated herein by reference, are particularly useful for delivery of a transgene to a neuronal cell, which has importance for those lysosomal storage diseases in which the enzymatic defect manifests in neuronal cells, e.g, Hurler Scheie, Hunter's, and Tay-Sach's diseases. AAV vectors, such as those disclosed in U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see Mah et al., Clin. Pharmacokinet. 2002; 41(12):901-11; Scott et al., Neuromuscul. Disord. 2002;12 Suppl 1:S23-9. In addition, see U.S. Pat. No. 5,670,488.

The coding sequences of the gene to be delivered are operably linked to expression control sequences, e.g., a promoter that directs expression of the gene. As used herein, the phrase "operatively linked" refers to the functional relationship of a polynucleotide/gene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

In one specific embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA 1989, 86:8932-8935; Zijlstra et al., Nature 1989, 342: 435-438; U.S. Pat. No. 6,244,113 to Zarling et al.; and U.S. Pat. No. 6,200,812 to Pati et al.)

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

Direct transfer. In a specific embodiment, the vector is directly administered in vivo, where it enters the cells of the organism and mediates expression of the gene. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-β-1-64-N-acetylglucosamine polysaccharide; see U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem. 1987, 62:4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., Mol. Therapy 2000, 2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Recently, a technique referred to as magnetofection has been used to deliver vectors to mammals. This technique associates the vectors with superparamagnetic nanoparticles for delivery under the influence of magnetic fields. This application reduces the delivery time and enhances vector efficacy (Scherer et al., Gene Therapy 2002; 9:102-9). Additional targeting and delivery methodologies are contemplated in the description of the vectors, below.

In a specific embodiment, the nucleic acid can be administered using a lipid carrier. Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 1989; 337:387). Intravenous injection of cationic lipid-plasmid complexes into mice has been shown to result in expression of the DNA in lung (Brigham et al., Am. J. Med. Sci. 1989; 298:278). See also, Osaka et al., J. Pharm. Sci. 1996; 85(6): 612-618; San et al., Human Gene Therapy 1993; 4:781-788; Senior et al., Biochemica et Biophysica Acta 1991; 1070:173-179); Kabanov and Kabanov, Bioconjugate Chem. 1995; 6:7-20; Liu et al., Pharmaceut. Res. 1996; 13; Remy et al., Bioconjugate Chem. 1994; 5:647-654; Behr, J-P., Bioconjugate Chem 1994; 5:382-389; Wyman et al., Biochem. 1997; 36:3008-3017; U.S. Pat. No. 5,939,401 to Marshall et al; U.S. Pat. No. 6,331,524 to Scheule et al.

Representative cationic lipids include those disclosed, for example, in U.S. Pat. No. 5,283,185; and e.g., U.S. Pat. No. 5,767,099, the disclosures of which are incorporated herein by reference. In a preferred embodiment, the cationic lipid is $N_4$-spermine cholesteryl carbamate (GL-67) disclosed in U.S. Pat. No. 5,767,099. Additional preferred lipids include $N_4$-spermidine cholestryl carbamate (GL-53) and 1-($N_4$-spermine)-2,3-dilaurylglycerol carbamate (GL-89)

Preferably, for in vivo administration of viral vectors, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors. In that regard, it is advantageous to employ a viral vector that is engineered to express a minimal number of antigens.

Indirect transfer. Somatic cells may be engineered ex vivo with a construct encoding a wild-type protein using any of the methods described above, and re-implanted into an individual. This method is described generally in WO 93/09222 to Selden et al. In addition, this technology is used in Cell Based Delivery's proprietary ImPACT technology, described in Payumo et al., Clin. Orthopaed. and Related Res. 2002; 403S: S228-S242. In such a gene therapy system, somatic cells (e.g., fibroblasts, hepatocytes, or endothelial cells) are removed from the patient, cultured in vitro, transfected with the gene(s) of therapeutic interest, characterized, and reintroduced into the patient. Both primary cells (derived from an individual or tissue and engineered prior to passaging), and secondary cells (passaged in vitro prior to introduction in vivo) can be used, as well as immortalized cell lines known in the art. Somatic cells useful for the methods of the present invention include but are not limited to somatic cells, such as fibroblasts, keratinocytes, epithelial cells, endothelial cells, glial cells, neural cells, formed elements of the blood, muscle cells, other somatic cells that can be cultured, and somatic cell precursors. In a preferred embodiment, the cells are fibroblasts or mesenchymal stem cells.

Nucleic acid constructs, which include the exogenous gene and, optionally, nucleic acids encoding a selectable marker, along with additional sequences necessary for expression of the exogenous gene in recipient primary or secondary cells, are used to transfect primary or secondary cells in which the encoded product is to be produced. Such constructs include but are not limited to infectious vectors, such as retroviral, herpes, adenovirus, adenovirus-associated, mumps and poliovirus vectors, can be used for this purpose.

Transdermal delivery is especially suited for indirect transfer using cell types of the epidermis including keratinocytes, melanocytes, and dendritic cells (Pfutzner et al., Expert Opin. Investig. Drugs 2000; 9:2069-83).

Mesenchymal stem cells (MSCs) are non-blood-producing stem cells produced in the bone marrow. MSCs can be made to differentiate and proliferate into specialized non-blood tissues. Stem cells transfected with retroviruses are good candidates for the therapy due to their capacity for self-renewal. This ability precludes repetitive administration of the gene therapy. Another advantage is that if the injected stem cells reach the target organ and then differentiate, they can replace the damaged or malformed cells at the organ.

Gene Therapy in Lysosomal Storage Disorders. Recently, recombinant gene therapy methods are in clinical or preclinical development for the treatment of lysosomal storage disorders, see, e.g., U.S. Pat. No. 5,658,567 issued Aug. 19, 1997 for recombinant alpha-galactosidase A therapy for Fabry disease; U.S. Pat. No. 5,580,757 issued Dec. 3, 1996 for Cloning and Expression of Biologically Active α-galactosidase A as a Fusion Protein; U.S. Pat. No. 6,066,626, issued May 23, 2000 for Compositions and method for treating lysosomal storage disease; U.S. Pat. No. 6,083,725, issued Jul. 4, 2000 for Transfected human cells expressing human alphα-galactosidase A protein; U.S. Pat. No. 6,335,011, issued Jan. 1, 2002 for Methods for delivering DNA to muscle cells using recombinant adeno-associated virus virions to treat lysosomal storage disease; Bishop, D. F. et al., Proc. Natl. Acad. Sci., USA. 1986; 83:4859-4863; Medin, J. A. et al., Proc. Natl. Acad. Sci., USA. 1996; 93:7917-7922; Novo, F. J., Gene Therapy 1997; 4:488-492; Ohshima, T. et al., Proc. Natl. Acad. Sci., USA. 1997; 94:2540-2544; Sugimoto Y. et al., Human Gene Therapy 1995; 6:905-915; Sly et al., Proc. Natl. Acad. Sci. USA. 2002;99(9):5760-2; Raben et al., Curr. Mol. Med 0.2002; 2(2):145-66; Eto et al., Curr. Mol. Med. 2002; 2(1):83-9; Vogler et al., Pediatr. Dev. Pathol. 2001; 4(5):421-33; Barranger et al., Expert Opin. Biol. Ther. 2001; 1(5):857-67; Yew et al., Curr. Opin. Mol. Ther. 2001; 3(4):399-406; Caillaud et al., Biomed. Pharmacother. 2000; 54(10):505-12 and Ioannu et al., J. Am. Soc. Nephrol. 2000; 11(8):1542-7.

In 2002, Brooks et al. demonstrated that gene transfer of β-glucuronidase into a mouse model of MPS VII using a feline leukemia virus, corrected associated CNS deficits (PNAS 2002; 99: 6216-6221). Indirect transfer of encapsulated Madin-Darby canine kidney cells that were genetically modified to express canine alpha-iduronidase, and implanted into dog brains under steoreotaxic guidance, was demonstrated to be efficacious in a dog model of MPS (Barsoum et al., J Lab Clin Med. 2003;142(6):399-413).

Active Site-Specific Chaperones

ASSCs contemplated by the present invention include but are not limited to small molecules (e.g., organic or inorganic molecules which are less than about 2 kD in molecular weight, are more preferably less than about 1 kD in molecular weight), including substrate or binding partner mimetics; small ligand-derived peptides or mimetics thereof; nucleic acids such as DNA, RNA; antibodies, including Fv and single chain antibodies, and Fab fragments; other macromolecules (e.g., molecules greater than about 2 kD in molecular weight) and members of libraries derived by combinatorial chemistry, such as molecular libraries of D- and/or L-configuration amino acids; phosphopeptides, such as members of random or partially degenerate, directed phosphopeptide libraries (see, e.g., Songyang et al., Cell 1993, 72:767-778).

Synthetic libraries (Needels et al., Proc. Natl. Acad. Sci. USA 1993, 90:10700-4; Ohlmeyer et al., Proc. Natl. Acad. Sci. USA 1993, 90:10922-10926; Lam et al., PCT Publication No. WO 92/00252; Kocis et al., PCT Publication No. WO 9428028) and the like provide a source of ASSCs according to the present invention. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available, e.g., from Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

U.S. patent application Ser. No. 10/377,179, filed Feb. 28, 2003 and incorporated herein by reference, describes screening methods for ASSC's for misfolded proteins.

In a preferred embodiment, small molecules useful for the present invention are inhibitors of lysosomal enzymes and include glucose and galactose imino sugar derivatives as described in Asano et al., J. Med. Chem 1994; 37:3701-06; Dale et al., Biochemistry 1985; 24:3530-39; Goldman et al., J. Nat. Prod. 1996; 59:1137-42; Legler et al, Carbohydrate Res. 1986; 155:119-29; and Okumiya et al., Biochem. Biophys. Res. Comm. 1995; 214:1219-240. Such derivatives include but are not limited those compound listed in Table 1.

Other ASSCs can be those mentioned above, e.g., small synthetic compounds, which were found to stabilize mutant forms of p53 (Foster et al., Science 1999; 286:2507-10); small molecule receptor antagonists and ligands, which were found to stabilize receptors (Morello et al., J. Clin. Invest. 2000; 105: 887-95; Petaja-Repo et al., EMBO J. 2002; 21:1628-37); and drugs or substrates, which were found to stabilize channel proteins and transporters (Rajamani et al., Circulation 2002; 105:2830-5; Zhou et al., J. Biol. Chem. 1999; 274:31123-26; Loo et al., J. Biol. Chem. 1997; 272: 709-12).

In another embodiment, ASSC's useful in the method of the present invention are activators of cystic fibrosis transmembrane conductance regulator and, are identified using physical, and biochemical means (Blondelle et al., TIBTech 1996, 14:60).

In another preferred embodiment, ASSC's useful for the present invention are ligands of G protein-coupled receptors, such as δ opioid receptor, V2 vasopressin receptor, and photopigment rhodopsin, as described in Petaja-Repo et al., EMBO J. 2002; 21: 1628-37; Morello et al., J. Clin. Invest.2000; 105: 887-95; Saliba et al., J. Cell Sci. 2002; 115: 2907-18.

In yet another preferred embodiment, ASSC's useful for the present invention are blockers of ion channel proteins, such as HERG potassium channel in human Long QT syndrome, pancereatic ATP-sensitive potassium (KATP) channel in familial hyperinsulinism, as described in Zhou et al., J. Biol. Chem. 1999; 274: 31123-26; Taschenberger et al., J. Biol. Chem. 2002; 277: 17139-46.

Formulations and Administration

ASSCs. The ASSCs to be administered to an individual with a recombinant gene may be formulated for administration by, e.g., oral, parenteral, transdermal, or transmucosal routes, depending on whether the chaperone is a small molecule, synthetic compound, or protein or peptide.

For oral administration, e.g., for small molecules, the pharmaceutical compositions may take the form of tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils);

and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the chaperones for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The ASSCs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the ASSCs may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Recombinant gene. As described above, there are several methods known in the art for delivering naked DNA to individuals, including direct injection into the target tissue, e.g., intramuscular, use of cationic lipid carriers, by intravenous infusion or inhalation. See the gene therapy disclosure above.

For administration of somatic cells engineered to overexpress the recombinant gene product, the cells may be introduced into an individual, through various standardized routes of administration, so that they will reside in, for example, the renal subcapsule, a subcutaneous compartment, the central nervous system, the intrathecal space, the liver, the intraperitoneal cavity, or within a muscle. The cells may also be injected intravenously or intra-arterially so that they circulate within the individual's bloodstream.

The cells may alternatively be embedded in a matrix or gel material, such as described in U.S. Pat. No. 5,965,125 to Mineau-Hanschke, which describes the use of hybrid matrix implants, or in Jain et al. (PCT application WO 95/19430), which describes macroencapsulation of secretory cells in a hydrophilic gel material (each of which is hereby incorporated by reference).

The number of genetically modified cells will depend on the individual's weight, age, and clinical status, and can be routinely determined by those skilled in the art. In one embodiment, about $1\times10^6$ and $1\times10^9$ cells/day will be used.

Timing. Administration of the ASSC according to the present invention will generally follow delivery of the gene, to allow for expression of the recombinant protein by the target cells/tissue. Since the expression of the gene will be sustained for a period of time, for as long as the gene is expressible, the ASSC will be remained effective as a chaperone and stabilizer for the recombinant protein. Therefore, administration of ASSC will be necessary for the same period as the gene is expressed.

In an embodiment where the ASSC has a short circulating half-life (e.g., a small molecule), the ASSC will be orally administered continuously, such as daily, in order to maintain a constant level in the circulation. Such a constant level will be one that has been determined to be non-toxic to the patient, and optimal regarding interaction with the protein, which will be continuously produced, to confer a non-inhibitory, therapeutic effect.

In the event that the therapeutic gene supplements inadequate activity of an endogenous mutant gene, the timing of chaperone delivery becomes less significant since the effective amount can enhance the activity of the endogenous mutant as well as increase the efficiency of the therapeutic gene.

In vivo stability. The presence of an ASSC for the protein encoded by the administered gene will have the benefit of improving the efficiency of protein processing during synthesis in the ER (i.e. by preventing aggregation), and prolonging in the circulation and tissue the half-life of the protein, thereby maintaining effective protein levels over longer time periods. This will result in increased expression in clinically affected tissues. This confers such beneficial effects to the patient as enhanced relief, reduction in the frequency of treatment, and/or reduction in the amount of gene administered. This will also reduce the cost of treatment.

In addition to stabilizing the expressed protein, the ASSC will also stabilize and enhance expression of any endogenous mutant proteins that are deficient as a result of mutations that prevent proper folding and processing in the ER, as in conformational disorders such as the LSDs.

Dosages

The effective amount of ASSC to be administered with the recombinant gene will depend, in part, on the method of delivery, specific amount and typical expression level of the recombinant gene administered. The specific effective amount can be determined on a case-by-case basis, depending on the protein and corresponding ASSC, by those skilled in the art. The variation depends, for example, on the patient and the recombinant gene and ASSC used. Other factors to consider in determining doses are the individual's age, weight, sex, and clinical status. Pharmacokinetic and pharmacodynamics such as half-life ($t_{1/2}$), peak plasma concentration ($c_{max}$) time to peak plasma concentration ($t_{max}$), exposure as measured by area under the curve (AUC) and tissue distribution for both the protein and the ASSC, as well as data for ASSC-replacement protein binding (affinity constants, association and dissociation constants, and valency), can be obtained using ordinary methods known in the art to determine compatible amounts required in a dosage form to confer a therapeutic effect.

Data obtained from cell culture assay or animal studies may be used to formulate a range of dosages for use in humans. The dosage of compounds used in therapeutic methods of the present invention preferably lie within a range of circulating concentrations that includes the $ED_{50}$ concentration (effective for 50% of the tested population) but with little or no toxicity (e.g., below the $LD_{50}$ concentration). The particular dosage used in any application may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

Toxicity and therapeutic efficacy of the composition can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$. Chaperone compounds that exhibit large therapeutic indices are preferred.

The concentrations of the ASSC will be determined according to the amount required to stabilize the protein in vivo, in tissue or circulation, without preventing its activity. For example, where the ASSC is an enzyme inhibitor, the concentration of the inhibitor can be determined by calculating the $IC_{50}$ value of the ASSC for the enzyme. Concentrations below the $IC_{50}$ value can then be evaluated based on effects on enzyme activity, e.g., the amount of inhibitor needed to increase the amount of enzyme activity or prolong enzyme activity of the administered enzyme. The $IC_{50}$ value of the compound deoxygalactonojiromycin (DGJ) for the α-Gal A enzyme is 0.04 µM, indicating that DGJ is a potent inhibitor. Accordingly, it is expected that the concentration of α-Gal A would be much lower than that of the α-Gal A administered. See Examples below.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Intracellular Enhancement of α-Gal A with ASSCs

Methods. The COS-7 cells are transfected with pCNX2-AGA according the protocol established previously (Ishii et al. Arch. Biochem. Biophys. 2000; 377:228-233) using FuGene 6 Transfection Reagent.

The wild type enzyme is expressed in the transfected COS-7 cells. After the transfection, the cells are cultured in methionine- and cysteine-free medium that is supplemented with a [$^{35}$S]-Protein Labeling Mix (New England Nuclear, Boston, Mass.) with or without DGJ for 30 min. The medium is replaced with non-radioactive medium with or without DGJ, and the cells are cultured for an additional period. The [$^{35}$S]-labeled proteins are extracted using 1% Triton X -100 over the time, and the extent of intracellular process and amount of α-Gal A is determined following immunoprecipitation with anti-α-Gal A IgG and SDS-PAGE.

Results. The amount of [$^{35}$S]-labeled α-Gal A is expected to be larger in the cells cultured with DGJ than those obtained in the culture without DGJ, indicating that the ASSC (DGJ) increases the effectiveness of processing of the protein in the ER. The [$^{35}$S]-labeled α-Gal A is also expected to remain longer in the cells cultured with DGJ than those in the cells cultured in the absence of DGJ, indicating that the ASSC (DGJ) prevents the intracellular degradation of α-Gal A. These results will indicate that the ASSC can be effective in a combination with gene therapy.

Example 2

Co-administration of DGJ to Fabry Mice Treated Using Gene Therapy

Methods. α-Gal A deficient mice (Fabry KO mice) have been generated previously (Oshima et al., Proc. Natl. Acad. Sci. USA 1997; 94: 2540-254) and gene therapy has been tested on these knockout mice (Takahashi et al., Proc. Natl. Acad. Sci. USA 2002; 99:13777-82; Siatskas et al., J. Inherit. Metab. Dis. 2001; 24: 25-41; Ziegler et al., Hum. Gene. Ther. 2002; 13, discussion 11-2: 935-45). These experiments showed that the gene therapy could be useful for the treatment of Fabry disease. Co-administration of DGJ to the mice treated with gene therapy will increase the efficiency of the gene therapy, since it significantly improves the expression of the therapeutic gene product, specifically by preventing aggregation in the ER of the target cell. The KO mice following the gene therapy protocol receive DGJ dissolved in drinking water and the α-Gal A activity in various tissues including heart, kidney, spleen, liver, and lung as well as serum is determined over a period of time, and compared with those from the control mice that do not receive DGJ, and to mice that receive DGJ but not the gene therapy. The higher enzyme activity and longer remaining time indicate that co-administration of the ASSC can improve the efficiency of gene therapy.

\* \* \* \* \*

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of improving gene therapy by increasing the level of expression of a recombinant protein corresponding to an individual's endogenous protein in vivo in cells of an individual, wherein the recombinant protein is expressed from an expression vector which has been introduced into the cells, which method comprises administering to the individual an active site-specific chaperone of the protein, with the proviso that the individual's endogenous protein is not a mutant protein that is deficient due to defective folding or processing in the endoplasmic reticulum.

2. The method of claim 1, wherein the vector is a viral vector.

3. The method of claim 2, wherein the viral vector is an adenoviral vector.

4. The method of claim 1, wherein the protein is an enzyme and the active site-specific chaperone is a reversible competitive inhibitor of the enzyme.

5. The method of claim 4, wherein the enzyme is α-galactosidase A.

6. The method of claim 4, wherein the enzyme is β-glucocerebrosidase.

7. The method of claim 5, wherein the reversible competitive inhibitor is a compound of the following formula:

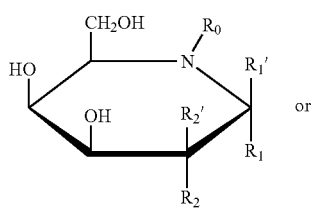

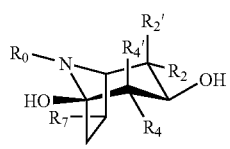

wherein $R_0$ represents H or a $C_1$-$C_{12}$ alkyl chain;

$R_1$ and $R_1'$ independently represent H, OH, a 1-4 carbon alkyl alkoxy or hydroxyalkyl group;

$R_2$ and $R_2'$ independently represent H, OH or a $C_1$-$C_{12}$ alkyl group $R_4$ and $R_4'$ independently represent H, OH; and $R_7$ represents H or OH.

8. The method of claim 7, wherein the reversible competitive inhibitor is a compound selected from the group consisting of 1-deoxygalactonojirimycin, α-allo-homonojirmycin, α-galacto-homonojirmycin, α-1-C-butyl-deoxynojirimycin, calystegine $A_3$, calystegine $B_2$, N-methyl-calystegine $A_3$, and N-methyl-calystegine $B_2$.

9. The method of claim 7, wherein the reversible competitive inhibitor is 1-deoxygalactonojirimycin.

10. The method of claim 6, wherein the reversible competitive inhibitor is a compound of the following formula:

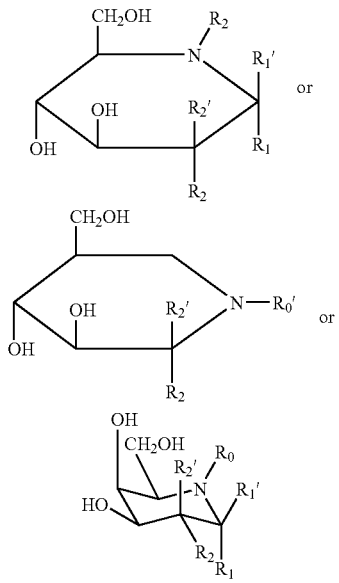

wherein $R_0$ represents H or a $C_1$-$C_{12}$ alkyl chain;

$R_0'$ represents H, a straight chain or branched saturated carbon chain containing 1-12 carbon atoms, optionally substituted with a phenyl, hydroxyl or cyclohexyl group;

$R_1$ and $R_1'$ independently represent H, OH, a 1-4 carbon alkyl, alkoxy or hydroxyalkyl group; and $R_2$ and $R_2'$ independently represent H, OH or a $C_1$-$C_{12}$ alkyl group.

11. The method of claim 10, wherein the reversible competitive inhibitor is a compound selected from the group consisting of isofagomine, N-dodecyl-isofagomine, N-nonyl-isofagomine, N-dodecyl-deoxynojirimycin, calystegine $A_3$, calystegine $B_2$, calystegine $B_3$ and calystegine $C_1$.

12. The method of claim 11, wherein the reversible competitive inhibitor is isofagomine.

13. The method of claim 11, wherein the reversible competitive inhibitor is N-dodecyl-isofagomine.

14. A method of improving gene therapy in an individual by increasing the level of expression of a recombinant protein corresponding to an individual's endogenous protein in vivo, wherein the recombinant protein is expressed by host cells comprising an expression vector encoding the recombinant protein, which method comprises co-administering to the individual the host cells and an effective amount of an active-site specific chaperone of the protein, with the proviso that the individual's endogenous protein is not a mutant protein that is deficient due to defective folding or processing in the endoplasmic reticulum.

15. The method of claim 14, wherein the vector is a viral vector.

16. The method of claim 15, wherein the viral vector is an adenoviral vector.

17. The method of claim 15, wherein the host cells are human primary cells and the individual is a human.

18. The method of claim 17, wherein the human cells are mesenchymal stem cells.

19. The method of claim 14, wherein the protein is an enzyme.

20. The method of claim 19 wherein the enzyme is α-galactosidase A.

21. The method of claim 19, wherein the enzyme is β-glucocerebrosidase.

22. The method of claim 20, wherein the reversible competitive inhibitor is a compound of the following formula:

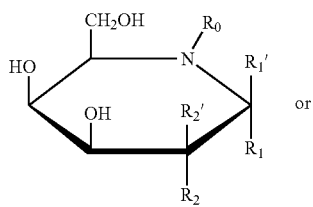

or

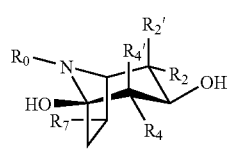

wherein $R_0$ represents H or a $C_1$-$C_{12}$ alkyl chain;

$R_1$ and $R_1'$ independently represent H, OH, a 1-4 carbon alkyl, alkoxy or hydroxyalkyl group;

$R_2$ and $R_2'$ independently represent H, OH or a $C_1$-$C_{12}$ alkyl group $R_4$ and $R_4'$ independently represent H, OH; and $R_7$ represents H or OH.

23. The method of claim 22, wherein the reversible competitive inhibitor is a compound selected from the group consisting of 1-deoxygalactonojirimycin, α-allo-homonojirimycin, α-galacto-homonojirimycin, α-1-C-butyl-deoxynojirimycin, calystegine $A_3$, calystegine $B_2$, N-methyl-calystegine $A_3$, and N-methyl-calystegine $B_2$.

24. The method of claim 23, wherein the reversible competitive inhibitor is 1-deoxygalactonojirimycin.

25. The method of claim 21, wherein the reversible competitive inhibitor is a compound of the following formula:

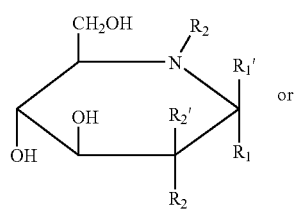

or

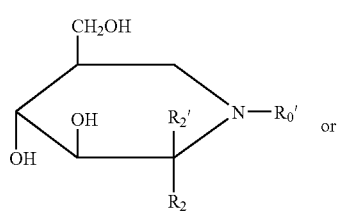

or

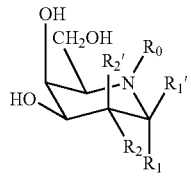

wherein $R_0$ represents H or a $C_1$-$C_{12}$ alkyl chain;

$R_0'$ represents H, a straight chain or branched saturated carbon chain containing 1-12 carbon atoms, optionally substituted with a phenyl, hydroxyl or cyclohexyl group;

$R_1$ and $R_1'$ independently represent H, OH, a 1-4 carbon alkyl, alkoxy or hydroxyalkyl group; and $R_2$ and $R_2'$ independently represent H, OH or a $C_1$-$C_{12}$ alkyl group.

26. The method of claim 25, wherein the reversible competitive inhibitor is a compound selected from the group consisting of isofagomine, N-dodecyl-isofagomine, N-nonyl-isofagomine, N-dodecyl-deoxynojirimycin, calystegine $A_3$, calystegine $B_2$, calystegine $B_3$ and calystegine $C_1$.

27. The method of claim 26, wherein the reversible competitive inhibitor is isofagomine.

28. The method of claim 26, wherein the reversible competitive inhibitor is N-dodecyl-isofagomine.

29. A method of improving treatment in an individual being administered a therapeutic vector comprising a gene encoding a protein corresponding to an individual's endogenous protein, comprising co-administering to the individual an active site-specific chaperone for the protein, with the proviso that the individual's endogenous protein is not a mutant, endogenous protein that is deficient due to defective folding or processing in the endoplasmic reticulum.

30. The method of claim 29, wherein the protein is an enzyme and the active site-specific chaperone is an inhibitor of the enzyme.

31. The method of claim 30 wherein the enzyme is associated with a lysosomal storage disorder.

32. The method of claim 31, wherein the enzyme is α-galactosidase A.

33. The method of claim 31, wherein the enzyme is β-glucocerebrosidase.

34. The method of claim 32, wherein the reversible competitive inhibitor is a compound of the following formula:

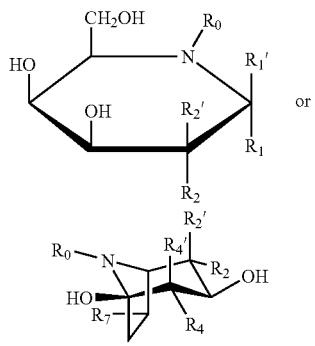

wherein $R_0$ represents H or a $C_1$-$C_{12}$ alkyl chain;

$R_1$ and $R_1'$ independently represent H, OH, a 1-4 carbon alkyl, alkoxy or hydroxyalkyl group;

$R_2$ and $R_2'$ independently represent H, OH or a $C_1$-$C_{12}$ alkyl group $R_4$ and $R_4'$ independently represent H, OH; and $R_7$ represents H or OH.

35. The method of claim 34, wherein the reversible competitive inhibitor is a compound selected from the group consisting of 1-deoxygalactonojirimycin, α-allo-homonojirimycin, α-galacto-homonojirimycin, α-1-C-butyl-deoxynojirimycin, calystegine $A_3$, calystegine $B_2$, N-methyl-calystegine $A_3$, and N-methyl-calystegine $B_2$.

36. The method of claim 35, wherein the reversible competitive inhibitor is 1-deoxygalactonojirimycin.

37. The method of claim 33, wherein the reversible competitive inhibitor is a compound of the following formula:

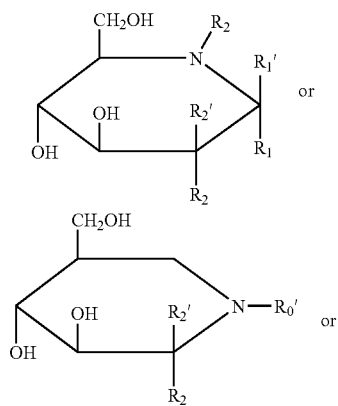

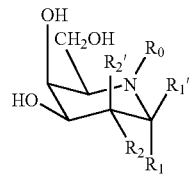

wherein $R_0$ represents H or a $C_1$-$C_{12}$ alkyl chain;

$R_0'$ represents H, a straight chain or branched saturated carbon chain containing 1-12 carbon atoms, optionally substituted with a phenyl, hydroxyl or cyclohexyl group;

$R_1$ and $R_1'$ independently represent H, OH, a 1-4 carbon alkyl, alkoxy or hydroxyalkyl group; and $R_2$ and $R_2'$ independently represent H, OH or a $C_1$-$C_{12}$ alkyl group.

38. The method of claim 37, wherein the reversible competitive inhibitor is a compound selected from the group consisting of isofagomine, N-dodecyl-isofagomine, N-nonyl-isofagomine, N-dodecyl-deoxynojirimycin, calystegine $A_3$, calystegine $B_2$, calystegine $B_3$ and calystegine $C_1$.

39. The method of claim 38, wherein the reversible competitive inhibitor is isofagomine.

40. The method of claim 38, wherein the reversible competitive inhibitor is N-dodecyl-isofagomine.

* * * * *